US009234849B2

(12) United States Patent
Trupke et al.

(10) Patent No.: US 9,234,849 B2
(45) Date of Patent: *Jan. 12, 2016

(54) METHOD AND SYSTEM FOR INSPECTING INDIRECT BANDGAP SEMICONDUCTOR STRUCTURE

(75) Inventors: Thorsten Trupke, Coogee (AU); Robert Andrew Bardos, North Bondi (AU)

(73) Assignee: BT IMAGING PTY LIMITED, Surry Hills (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/494,373

(22) Filed: Jun. 12, 2012

(65) Prior Publication Data

US 2012/0257044 A1 Oct. 11, 2012

Related U.S. Application Data

(63) Continuation of application No. 13/273,697, filed on Oct. 14, 2011, now Pat. No. 8,218,140, and a continuation of application No. 12/083,429, filed as application No. PCT/AU2006/001420 on Oct. 11, 2006, now Pat. No. 8,064,054.

(30) Foreign Application Priority Data

Oct. 11, 2005 (AU) .................. 2005905598

(51) Int. Cl.
*G01J 3/40* (2006.01)
*G01N 21/64* (2006.01)
(Continued)

(52) U.S. Cl.
CPC ......... *G01N 21/6489* (2013.01); *F21Y 2101/02* (2013.01); *G01N 21/6456* (2013.01); *G01N 2021/8887* (2013.01)

(58) Field of Classification Search
CPC ................. G01J 3/02; G01J 3/14; G01J 3/28; G01J 3/40; G01N 21/31
USPC ........................... 356/30, 301, 302
See application file for complete search history.

(56) References Cited

U.S. PATENT DOCUMENTS 4,661,770 A 4/1987 von
4,713,140 A 12/1987 Tien
(Continued)

FOREIGN PATENT DOCUMENTS

DE  10 2005 040 010 A1  3/2007
EP         211590 A2    2/1987
(Continued)

OTHER PUBLICATIONS

Alt, H et al., "Contrast phenomena of band-band and deep level photoluminescence topographs in annealed semi-insulating GaAs", Appl. Phys. Lett. 55(19), pp. 172-174 (Nov. 6, 1989).
(Continued)

*Primary Examiner* — Abdullahi Nur
(74) *Attorney, Agent, or Firm* — Mattingly & Malur, PC

(57) ABSTRACT

Methods (600) and systems (100) for inspecting an indirect bandgap semiconductor structure (140) are described. A light source (110) generates light (612) suitable for inducing photoluminescence in the indirect bandgap semiconductor structure (140). A short-pass filter unit (114) reduces long-wavelength light of the generated light above a specified emission peak. A collimator (112) collimates (616) the light. A large area of the indirect bandgap semiconductor structure (140) is substantially uniformly and simultaneously illuminated (618) with the collimated, short-pass filtered light. An image capture device (130) captures (620) images of photoluminescence simultaneously induced by the substantially uniform, simultaneous illumination incident across the large area for the indirect bandgap semiconductor structure. The photoluminescence images are image processed (622) to quantify spatially resolved specified electronic properties of the indirect bandgap semiconductor structure (140) using the spatial variation of the photoluminescence induced in the large area.

32 Claims, 5 Drawing Sheets

(51) Int. Cl.
*F21Y 101/02* (2006.01)
*G01N 21/88* (2006.01)

(56) References Cited

U.S. PATENT DOCUMENTS

| | | | |
|---|---|---|---|
| 5,302,832 A | 4/1994 | Kitagawara et al. | |
| 5,381,016 A | 1/1995 | Moriya | |
| 5,568,978 A * | 10/1996 | Johnson et al. | 374/161 |
| 6,429,968 B1 | 8/2002 | Carver | |
| 6,509,960 B2 | 1/2003 | Johnson et al. | |
| 6,894,773 B2 | 5/2005 | Morioka et al. | |
| 7,113,276 B1 | 9/2006 | Higgs et al. | |
| 7,446,868 B1 | 11/2008 | Higgs et al. | |
| 7,651,874 B2 | 1/2010 | Nagel | |
| 2003/0146109 A1 * | 8/2003 | Sailor et al. | 205/775 |
| 2004/0012775 A1 * | 1/2004 | Kinney et al. | 356/237.2 |
| 2004/0092042 A1 | 5/2004 | Higgs | |
| 2004/0263045 A1 | 12/2004 | Smith et al. | |
| 2007/0000434 A1 | 1/2007 | Buczkowski | |
| 2007/0008518 A1 * | 1/2007 | Hummel et al. | 356/237.1 |

FOREIGN PATENT DOCUMENTS

| | | |
|---|---|---|
| EP | 0 545 523 A2 | 6/1993 |
| EP | 416787 B1 | 5/1995 |
| EP | 1275954 A2 | 1/2003 |
| EP | 0 925 497 B1 | 2/2003 |
| GB | 2306640 B | 1/1998 |
| JP | 1-182738 A | 7/1989 |
| JP | 2031175 Y2 | 8/1990 |
| JP | 5-90368 A | 4/1993 |
| JP | 5-218163 A | 8/1993 |
| JP | 5281141 A | 10/1993 |
| JP | 8035934 A | 2/1996 |
| JP | 8054340 A | 2/1996 |
| JP | 9-230245 A | 9/1997 |
| JP | 2001500613 A | 1/2001 |
| JP | 2002107301 A | 10/2002 |
| JP | 2002-350732 A | 12/2002 |
| JP | 2003-4636 A | 1/2003 |
| JP | 2004526964 A | 9/2004 |
| JP | 2006-147848 A | 6/2006 |
| JP | 2006-178440 A | 7/2006 |
| WO | WO9811425 A1 | 3/1998 |
| WO | 00/03230 A1 | 1/2000 |
| WO | 02/40973 A2 | 5/2002 |
| WO | WO02077621 A1 | 10/2002 |

OTHER PUBLICATIONS

Arajawa, T. et al., "Fabrication and microscopic photoluminescence imaging of ridge-type InGaAs quantum wires grown on a (100) cleaved plane of AlGaAs/GaAs superlattice", Appl. Phys. Lett. 69(9), pp. 1294-1296 (Aug. 26, 1996).
Baeumler, M. et al., "Luminescence imaging—a well-established technique to study maternal-end device-related problems", Mat. Sci. Eng. B66, pp. 131-140 (1999).
Baumgartner, M. et al., "Characterization of si-GaAs wafer quality by room-temperature photoluminescence", Appl. Surf. Sci. 50, pp. 222-227 (1991).
Bernussi, A. et al., "Photoluminescence microscopy imaging of tensile strained In1-xGaxAsyP1-y/InP quantum wells grown by low-pressure metalorganic vapor phase epitaxy", Journal of Applied Physics, vol. 86, No. 1 (1999).
Black, J. et al., "Scanned-Laser Microscope for Photoluminescence Studies", Appl. Opt. vol. 1, No. 7, pp. 1553-1562 (Jul. 1972).
Carver, G., "Scanned photoluminescences with high spatial resolution in semi-insulating GaAs, and InP: aspects of surface passivation and photodegradation", Semicon, Sco. Technol. 7, pp. A53-A58 (1992).
Edelman, P. et al., "Photoluminescence and minority carrier diffusion length imaging in silcon and GaAs", Semicon. Sci. Technol. 7, pp. A22-A26 (1992).

Furstenberg, R. et al., "Apparatus for the imaging of infrared photoluminescence, transmittance, and phototransmittance with high spatial and spectral resolutions", Rev. Sci. Instrum. 77(7), 073101-1-073101-5 (2006).
Gourley, P. et al., "Controversy of critical layer thickness of InGaAs/GaAs strained-layer epitaxy", Appl. Plys. Lett. 52(5), pp. 377-379 (Feb. 1, 1998).
Hovel, H. "Scanned photoluminescence of semiconductors", Semicond. Sci. Technol. 7, pp. A1-A9 (1992).
Katsumata, T. et al., "Application of picosecond time resolved photoluminescence mapping for the characterization of semi-insulating GaAs wafers", J. Crystal Growth 103, pp. 14-20 (1990).
Livescu, G. et al., "A real-time photoluminescence imaging system", J. Electronic Materials 19(9), pp. 937-942 (1990).
Molva, E. et al., "Origin of microscpic inhomogeneities in bulk gallium arsenide", J. Crystal Growth 103, pp. 91-101 (1990).
Moore, C. et al., "A spatially resolved spectrally resolved photoluminescence mapping system", J. Crystal Growth 103, pp. 8-13 (1990).
Mori, Y. et al., "Two-dimensional image detection of luminescence and transport properties of GaAs", J. Crystal Growth 103, pp. 8-13 (1990).
Ostapenko, et al., "Defect mapping in full-size multi-crystalline Si wafers", Eur. Phys. J. Appl. Phys. 27, pp. 55-58 (2004).
Ostapenko S. et. al., "Defect monitoring using scanning photoluminescence spectroscopy in it multicrystalline silicon wafers", Semicond. Sci. Tech. 15, pp. 840-848 (2000).
Sartorius, B. et al., "Luminescence microscopy for quality control of material and processing", J. Crystal Growth 83, pp. 238-245 (1987).
Sochinskii, N. et al., "Infrared photoluminescence imaging of infrared materials: HgCdTe/Cd(Zn)Te heterostructures", Infrared Phys. Technol. 46, pp. 181-184 (2004).
Steiner, T. et al., "Cryogenic, whole wafer imaging of semi-insulating GaAs", Semicon. Sci. Technol 7, pp. A16-A21 (1992).
Tajima, M. "Characterization of semiconductors by photoluminescence mapping at room temperature", J. Crystal Growth 103, pp. 1-7 (1990).
Tarasov, I et al., "Defect passivation in multicrystalline silicon for solar cells", Appl. Phys. Lett. 85(19), pp. 4346-4348 (2004).
Toba, R. et al., "Surface characterization of semi-insulating GaAs wafers by room temperature photoluminescence mapping", Jr. Crystal Growth 103, 1990, pp. 28-37.
Vetter, T. et al., "Characterization of InP wafers by use of systems for high resolution photoluminescence imaging", J. Mater. Res. 6(5), pp. 1055-1060 (1991).
Wang, Z. et al., "Ambient and low temperature photoluminescence tophgraphy of GaAs substrates, epitaxial and implanted layers", Appl. Surf. Sci. 50, pp. 238-233 (1991).
Wang, Z. et al., :Photoluminescence microscopy investigation of lattice defect in epitaxial heterostructures, J. Crystal Growth 126, , pp. 205-215 (1993).
Wettling, W., "Direct and fast comparison of near-infrared absorption and photoluminescence topography of semiinsulating GaAs wafers", Appl. Phys. A 40, pp. 191-195 (1986).
L. Masarotto et al., Development of an UV Scanning Photoluminescence Apparatus for SiC Characterization:, Eur. Phys. J. AP 20, 141-144 (2002).
Search Report and Written Opinion, mailed Sep. 22, 2009 in Singapore Application No. 200802722.4.
L. Masarotta et al., Application of UV Scanning Photoluminescence Spectroscopy for Minority Carrier Lifetime Mapping, 349-352 Materials Science Forum 349-352 (Sep. 15, 2003).
Trupke, T. et al., "Photoluminescence: A Suprisingly Sensitive Lifetime Technology," Thirty-first IEEE Photovolataic Specialist Conference, Jan. 3, 2005, pp. 903-906, XP010822910.
Trupke, T. et al., "Photoluminescence imaging of silicon wafers," Applied Physics Letters, AIP, American Institute of Physica, Melville, NY, US, vol. 89, No. 4, Jul. 26, 2006, pp. 44107-044107, XP012088201, ISSN: 0003-6951, DOI: 10.1063/1.2234747.
Yagi, H., "Image Processing and Illumination," 6: Observing Micro-Objects, Eizojoho Industrial, Japan, Sangyo Kaihatsukiko Inc., Sep. 2000, vol. 32, No. 17, pp. 62-67.

(56) References Cited

OTHER PUBLICATIONS

Eurpoean Patent Office; Third Party Observation for application No. EP20060790291; Sep. 13, 2013; 22 pages total.

Japan Patent Office; Notice of Reasons for Rejection (English translation); Oct. 9, 2013; 3 pages total.

Ma et al.; "Study on defects in EMCZ-Si crystal by infrared light scattering tomography", Journal of Crystal Growth 208; 2000; pp. 282-288.

Nango et al., "An optical study on dislocation clusters in a slowly pulled silicon crystal"; Journal of Applied Physics; vol. 86, No. 11; Dec. 1, 1999; pp. 6000-6004.

A. Buczkowski et al.; "Photoluminescence Intensity Analysis in Application to Contactless Characterization of Silicon Wafers"; Journal of the Electrochemical Society, 150 (8); 2003; pp. G436-G442 (7 pages total); Salem, Oregon.

M. Green et al.; "Efficient silicon light-emitting diodes"; Nature; vol. 412, Aug. 28, 2001; pp. 805-808 (4 pages total); Macmillian Magazines Ltd.

T. Trupke et al.; "Very efficient light emission from bulk crystalline silicon"; Applied Physics Letters, vol. 82 No. 18; May 5, 2003; pp. 2996-2998 (3 pages total); American Institute of Physics.

P. J. Dean; "Photoluminescence as a Diagnostic of Semiconductors"; Progress in Crystal Growth and Characterization; 1982; vol. 6; 22 pages total; Great Britain.

H. Nakashima et al.; Photoluminescence topographic observation of defects in silicon crystals; Appl. Phys. Lett. 33 (6); Sep. 15, 1978; American Institute of Physics; 1 page total.

* cited by examiner

METHOD AND SYSTEM FOR INSPECTING INDIRECT BANDGAP SEMICONDUCTOR STRUCTURE

This is a continuation of U.S. patent application Ser. No. 13/273,697, which was filed in the United States Patent and Trademark Office on Oct. 14, 2011 and is a continuation of U.S. patent application Ser. No. 12/083,429. Said U.S. patent application Ser. No. 12/083,429 was filed in the United States Patent and Trademark Office on Jun. 12, 2008, as the U.S. National Phase of International Patent Application No. PCT/AU2006/001420 filed on Oct. 11, 2006, and issued on Nov. 22, 2011 as U.S. Pat. No. 8,064,054. Said International Patent Application No. PCT/AU2006/001420 published in the English language on Apr. 19, 2007, as International Patent Publication No. WO 2007/041758, and claims priority to Patent Application No. 2005905598 filed in Australia on Oct. 11, 2005. The contents of the foregoing applications, patents and patent publications are hereby incorporated by reference in their entireties.

TECHNICAL FIELD

The present invention relates generally to semiconductor testing and more particularly to testing of indirect bandgap semiconductor material.

BACKGROUND

Photovoltaic manufacturing is a rapidly expanding market with typical growth rates of greater than thirty percent (30%) per annum. The predominant sector of solar cell manufacturing is multi-crystalline wafer-based technology. In this industry, a significant proportion of total throughput is below specifications and is rejected, causing substantial financial losses to the industry each year. The production of a solar cell involves a highly specialized sequence of processing steps that starts with a bare semiconductor wafer, such as silicon.

Bel'kov, V V, et al, "Microwave-induced patterns in n-GaAs and their photoluminescence imaging", Physical Review B, Vol. 61, No. 20, *The American Physical Society*, 15 May 2000, pp. 13698-13702 describes a technique of photoluminescence (PL) imaging of n-GaAs. Photoluminescence is the light emitted by a semiconductor material in response to optical excitation. Using the photoluminescence imaging, self-organized patterns of high-electron density are contactlessly studied in the homogenous n-GaAs layers under homogeneous microwave irradiation. The n-GaAs contactless sample is housed in a rectangular waveguide, which has a metallic mesh window for observation, coupled to a microwave generator and is subjected to microwave irradiation. This assembly including the n-GaAs sample is cooled to 4.2 K in a bath cryostat containing liquid helium and illuminated uniformly with several red (620 nm) light emitting diodes (LEDs) organized in a ring. The cryostat has a window aligned with the metallic mesh window. A video camera is oriented facing the sample, with optics and an interference 820 nm (long-pass) filter interposed in that order between the cryostat window and the camera. The camera captures 3 mm×4 mm images, some of which show the formation of dark spots in the photoluminescence from the sample under microwave irradiation.

The system of Bel'kov can be used to test n-GaAs, which is a direct bandgap semiconductor, Given the high magnitude of photoluminescence efficiency in such a semiconductor the n-GaAs sample allows relatively low powered LEDs to be used as light sources for inducing photoluminescence, in which the source illumination diverges. Also, the arrangement of the waveguide and cryostat windows limits the viewing area of the camera. Disadvantageously, this only permits small areas (3 mm×7 mm) to be tested. Further, the system requires samples to be tested at low temperatures produced by a cryostat. The configuration of Bel'kov permits source illumination from the LEDs to be captured by the video camera. The long-pass filter is intended to block illumination from the LEDs and to transmit photoluminescence above 820 nm to the camera, but also transmits any illumination from the LEDs above 820 nm to the camera. For n-GaAs samples, the high efficiency photoluminescence generated greatly exceeds any undesired illumination from the LEDs. In view of these and other limitations, the system of Bel'kov is not suited for testing indirect bandgap semiconductors.

Masarotto, et al, "Development of an UV scanning photoluminescence apparatus for SiC characterization", Eur J AP 20, 141-144, 2002, describes an adapted scanning PL apparatus for characterizing SiC. PL mapping is obtained by scanning the sample using an x-y stage with a 1 µm step and a doubled $Ar^+$ laser beam focused by a microscope objective, with a spot diameter of 4 µm. Either integrated PL intensity or spectrally resolved PL can be obtained. This system scans PL in a point-by-point fashion. Such a system disadvantageously only permits a small area, i.e. a point, to be tested at any given time due to the scanning operation. Photoluminescence cannot be simultaneously captured across a large area of the sample under homogeneous illumination across the large area, which would better approximate operating conditions of a semiconductor device. Further, such a system is disadvantageously slow due to the scanning operation of the system.

A need therefore exists for an inspection system for indirect bandgap semiconductor structures, especially silicon, including bare or partially processed wafers that might otherwise result in a rejected solar cell.

SUMMARY

In accordance with an aspect of the invention, there is provided a method of inspecting an indirect bandgap semiconductor structure. The method comprises the steps of: generating light suitable for inducing photoluminescence in the indirect bandgap semiconductor structure; short-pass filtering the light to reduce long-wavelength light of the generated light above a specified emission peak; collimating the light; substantially uniformly and simultaneously illuminating a large area of the indirect bandgap semiconductor structure with the collimated, short-pass filtered light; capturing images of photoluminescence simultaneously induced by the substantially uniform, simultaneous illumination incident across the large area of the indirect bandgap semiconductor structure using an image capture device capable of capturing simultaneously the induced photoluminescence; and image processing the photoluminescence images to quantify spatially resolved, specified electronic properties of the indirect bandgap semiconductor structure using the spatial variation of said photoluminescence induced in said large area.

The indirect bandgap semiconductor may comprise silicon. The structure may comprise a bare or partially processed wafer of indirect bandgap semiconductor material, at least one partially formed electronic device, or a bare or partially processed silicon-on-insulator (SOI) structure. The electronic device may be a photovoltaic device.

The short-pass filtering step may be implemented using one or more short-pass filters. The short-pass filtering step may be implemented using dielectric mirrors, which reflect short wavelength light to be used and transmit unwanted long wavelength components. The short-pass filtering step may reduce by a factor of about 10 or more the total photon flux in a long-wavelength tail of the generated light, the long-wavelength tail beginning at a wavelength that is about ten percent (10%) higher than a longest wavelength emission peak of a source for generating the light.

The illuminated area of the indirect bandgap semiconductor structure may be equal to or greater than about 1.0 cm$^2$.

The method may further comprise the step of homogenizing the generated light.

The method may be performed at room temperature.

The generated light may be monochromatic or substantially monochromatic light. The light may be generated by at least one laser, laser diode, laser diode array, or high-powered light emitting diode (LED). Alternatively, the light may be generated by an array of light emitting diodes (LEDs) or a broad spectrum lamp and filtered to limit the spectrum of the light.

The total optical power of the light may exceed about 1 Watt.

A source of the generated light may be oriented toward the surface of one side of the structure for illumination of that surface and the image capture device is oriented toward the same surface for capturing the images of photoluminescence from that surface. Alternatively, a source of the generated light is oriented toward the surface of one side of the structure for illumination of that surface and an image capture device is oriented toward the surface of an opposite side of the structure for capturing the images of photoluminescence from the surface of the opposite side.

The method may further comprise the step of long pass filtering the photoluminescence induced in the silicon structure. The structure may act as long-pass filter of the incident light used for excitation of the photoluminescence. One or more long pass filters may be used in combination with the image capture device. The image capture device may comprise a focusing element and a focal plane array of light sensitive electronic elements. The focal plane array of light sensitive electronic elements may comprise an array of charge coupled devices (CCDs). The focal plane array may be made from silicon. The focal plane array of light sensitive electronic elements may be made from InGaAs. The focal plane array may be cooled.

The image capture device may comprise a pixel detector. The pixel detector may be a contact pixel detector coupled to a surface of the structure.

The image capture device may be a pixel detector or an array of charge coupled devices (CCDs), and a tapered fiber bundle may be coupled between a surface of the structure and the pixel detector or the CCD array.

The specified electronic properties comprise one or more of local defect densities, local shunts, local current-voltage characteristics, local diffusion length, and local minority carrier lifetime.

In accordance with another aspect of the invention, there is provided a system for inspecting an indirect bandgap semiconductor structure. The system comprises: a light source for generating light suitable for inducing photoluminescence in the indirect bandgap semiconductor structure; a short-pass filter unit disposed between the light source and the indirect bandgap semiconductor structure to reduce long-wavelength light of the generated light above a specified emission peak; a collimator disposed between the light source and the indirect bandgap semiconductor structure, the collimated, short-pass filtered light substantially uniformly and simultaneously illuminating a large area of the indirect bandgap semiconductor structure; an image capture device oriented towards the indirect bandgap semiconductor structure for capturing images of photoluminescence induced by said substantially uniform, simultaneous illumination incident across said large area of the indirect bandgap semiconductor structure by incident light.

The system may further comprise an image processor for processing the photoluminescence images to quantify spatially resolved, specified electronic properties of the indirect bandgap semiconductor structure.

The indirect bandgap semiconductor may comprise silicon. The structure may comprise a bare or partially processed wafer of indirect bandgap semiconductor material, at least one partially formed electronic device, or a bare or partially processed silicon-on-insulator (SOI) structure. The electronic device may be a photovoltaic device.

The short-pass filter unit may comprise one or more short-pass filters. The short-pass filter unit may comprise one or more dielectric mirrors, which reflect short wavelength light to be used and transmit unwanted long wavelength components. The short-pass filter unit may reduce by a factor of about 10 or more the total photon flux in a long-wavelength tail of the generated light, the long-wavelength tail beginning at a wavelength that is about ten percent (10%) higher than a longest wavelength emission peak of the light source for generating the light.

The illuminated area of the indirect bandgap semiconductor structure may be equal to or greater than about 1.0 cm$^2$.

The system may further comprise a beam homogenizer to homogenize the incident light across the illuminated area.

The system may inspect the indirect bandgap semiconductor sample at room temperature.

The generated light may be monochromatic or substantially monochromatic light.

The light source may comprise at least one laser, laser diode, laser diode array, or high-powered light emitting diode (LEDs), an array of light emitting diodes (LEDs), or a broad spectrum lamp in combination with one or more filters to limit the spectrum of the light.

The total optical power of the light may exceed about 1 Watt.

The light source may be oriented toward the surface of one side of the structure for illumination of that surface and the image capture device is oriented toward the same surface for capturing the images of photoluminescence from that surface. Alternatively, the light source may be oriented toward the surface of one side of the structure for illumination of that surface and the image capture device is oriented toward the surface of an opposite side of the structure for capturing the images of photoluminescence from the surface of the opposite side.

The structure may act as long-pass filter of the incident light used for excitation of the photoluminescence.

The system may further comprise one or more long pass filters for use in combination with the image capture device. The image capture device may comprise a focusing element and a focal plane array of light sensitive electronic elements. The focal plane array of light sensitive electronic elements may comprise an array of charge coupled devices (CCDs). The focal plane array may be made from silicon. The focal plane array of light sensitive electronic elements may be made from InGaAs. The focal plane array may be cooled.

The image capture device may comprise a pixel detector. The pixel detector may be a contact pixel detector coupled to a surface of the structure.

The image capture device may be a pixel detector or an array of charge coupled devices (CCDs), and may further comprise a tapered fiber bundle coupled between a surface of the structure and the pixel detector or the CCD array.

The specified electronic properties may comprise one or more of local defect densities, local shunts, local current-voltage characteristics, local diffusion length, and local minority carrier lifetime.

In accordance with yet another aspect of the invention, there is provided a method of inspecting a silicon structure. The method comprises the steps of: generating light suitable for inducing photoluminescence in the silicon structure; short-pass filtering the light to reduce long-wavelength light of the generated light above a specified emission peak; collimating the light; substantially uniformly and simultaneously illuminating a large area of one side of the silicon structure with the collimated, short-pass filtered light; and capturing images of photoluminescence simultaneously induced by said substantially uniform, simultaneous illumination incident across said large area of the silicon structure using an image capture device capable of capturing simultaneously said induced photoluminescence.

The method may further comprise the step of image processing the photoluminescence images to quantify spatially resolved, specified electronic properties of the silicon structure.

The structure comprises a bare or partially processed wafer of silicon material, at least partially formed photovoltaic device made from silicon, or a bare or partially processed silicon-on-insulator (SOI) structure.

The short-pass filtering step may be implemented using one or more short-pass filters. The short-pass filtering step may be implemented using dielectric mirrors, which reflect short wavelength light to be used and transmit unwanted long wavelength components.

The short-pass filtering step may reduce by a factor of about 10 or more the total photon flux in a long-wavelength tail of the generated light, the long-wavelength tail beginning at a wavelength that is about ten percent (10%) higher than a longest wavelength emission peak of a light source for generating the light.

The illuminated area of the silicon structure may be equal to or greater than about 1.0 cm$^2$.

The method may further comprise the step of homogenizing the generated light.

The method may be performed at room temperature.

The generated light may be monochromatic or substantially monochromatic light. The light may be generated by at least one laser, laser diode, laser diode array, high-powered light emitting diode (LED), an array of light emitting diodes (LEDs), or a broad spectrum lamp and filtered to limit the spectrum of the light.

The total optical power of the light may exceed about 1 Watt.

A source of the generated light may be oriented toward the surface of one side of the structure for illumination of that surface and an image capture device is oriented toward the same surface for capturing the images of photoluminescence from that surface. Alternatively, a source of the generated light is oriented toward the surface of one side of the structure for illumination of that surface and an image capture device is oriented toward the surface of an opposite side of the structure for capturing the images of photoluminescence from the surface of the opposite side.

The method may further comprise the step of long pass filtering the photoluminescence induced in the silicon structure. The structure may act as long-pass filter of the incident light used for excitation of the photoluminescence. One or more long pass filters may be used in combination with the image capture device. The image capture device may comprise a focusing element and a focal plane array of light sensitive electronic elements. The focal plane array of light sensitive electronic elements may comprise an array of charge coupled devices (CCDs). The focal plane array may be made from silicon. The focal plane array of light sensitive electronic elements may be made from InGaAs. The focal plane array may be cooled.

The image capture device may comprise a pixel detector. The pixel detector may be a contact pixel detector coupled to a surface of the structure.

The image capture device may be a pixel detector or an array of charge coupled devices (CCDs), and a tapered fiber bundle may be coupled between a surface of the structure and the pixel detector or the CCD array.

The specified electronic properties comprise one or more of local defect densities, local shunts, local current-voltage characteristics, local diffusion length, and local minority carrier lifetime.

In accordance with still another aspect of the invention, there is provided a system for inspecting a silicon structure. The system comprises: a light source for generating light suitable for inducing photoluminescence in the silicon structure; a short-pass filter unit disposed between the light source and the silicon structure to reduce long-wavelength light of the generated light above a specified emission peak; a collimator disposed between the light source and the silicon structure, short-pass filtered light substantially uniformly and simultaneously illuminating a large area of one side of the silicon structure; and an image capture device for capturing images of photoluminescence simultaneously induced by said substantially uniform, simultaneous illumination incident across the large area of the silicon structure by incident light.

The system may further comprise an image processor for processing the photoluminescence images to quantify spatially resolved, specified electronic properties of the silicon structure.

The structure may comprise a bare or partially processed wafer of silicon material, at least partially formed photovoltaic device made from silicon, or a bare or partially processed silicon-on-insulator (SOI) structure.

The short-pass filter unit may comprise one or more short-pass filters. The short-pass filter unit may comprise one or more dielectric mirrors, which reflect short wavelength light to be used and transmit unwanted long wavelength components.

The one or more short-pass filters reduce by a factor of about 10 or more the total photon flux in a long-wavelength tail of the generated light, the long-wavelength tail beginning at a wavelength that is about ten percent (10%) higher than a longest wavelength emission peak of a light source for generating the light.

The illuminated area of the silicon structure may be equal to or greater than about 1.0 cm$^2$.

The system may further comprise a homogenizer for homogenizing the generated light.

The system may inspect the silicon structure at room temperature.

The generated light may be monochromatic or substantially monochromatic.

The light source may be comprise at least one laser, laser diode, laser diode array, high-powered light emitting diode (LED), an array of light emitting diodes (LEDs), or a broad spectrum lamp and filtered to limit the spectrum of the light.

The total optical power of the light may exceed about 1 Watt.

The light source may be oriented toward the surface of one side of the silicon structure for illumination of that surface and the image capture device is oriented toward the same surface for capturing the images of photoluminescence from that surface. Alternatively, the light source may be oriented toward the surface of one side of the silicon structure for illumination of that surface and the image capture device is oriented toward the surface of an opposite side of the structure for capturing the images of photoluminescence from the surface of the opposite side.

The system may further comprise one or more long-pass filters for long pass filtering the light entering the image capture device.

The image capture device may comprise a focusing element and a focal plane array of light sensitive electronic elements. The focal plane array of light sensitive electronic elements may comprise an array of charge coupled devices (CCDs). The focal plane array may be made of silicon. The focal plane array of light sensitive electronic elements may be made from InGaAs. The focal plane array may be cooled.

The image capture device may comprise a pixel detector. The pixel detector may be a contact pixel detector coupled to a surface of the structure.

The image capture device may be a pixel detector or an array of charge coupled devices (CCDs), and may further comprise a tapered fiber bundle coupled between a surface of the structure and the pixel detector or the CCD array.

The specified electronic properties may comprise one or more of local defect densities, local shunts, local current-voltage characteristics, local diffusion length, and local minority carrier lifetime.

Other aspects of this system may be implemented in accordance with the details of the foregoing method.

BRIEF DESCRIPTION OF DRAWINGS

Embodiments of the invention are described hereinafter with reference to the drawings, in which.

DETAILED DESCRIPTION

Figure 1:
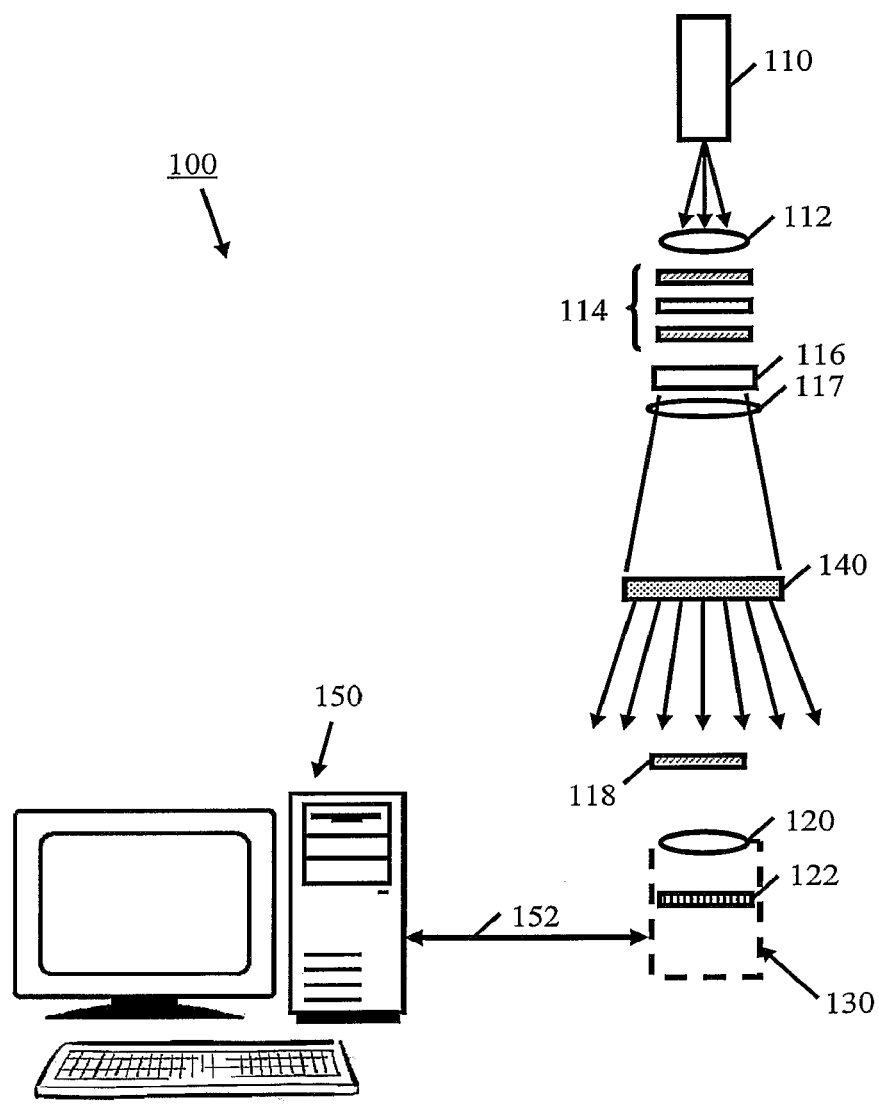
FIG. 1 is a block diagram of a system for inspecting an indirect bandgap semiconductor structure in accordance with an embodiment of the invention.

Methods and systems are disclosed for inspecting indirect bandgap semiconductor structures. In the following description, numerous specific details, including indirect bandgap semiconductor materials, image capture devices, and the like are set forth. However, from this disclosure, it will be apparent to those skilled in the art that modifications and/or substitutions may be made without departing from the scope and spirit of the invention. In other circumstances, specific details may be omitted so as not to obscure the invention.

Where reference is made in any one or more of the accompanying drawings to steps and/or features, which have the same or like reference numerals, those steps and/or features have for the purposes of this description the same function(s) or operation(s), unless the contrary intention appears.

In the context of this specification, the word "comprising" has an open-ended, non-exclusive meaning: "including principally, but not necessarily solely", but neither "consisting essentially of" nor "consisting only of". Variations of the word "comprising", such as "comprise" and "comprises", have corresponding meanings.

1. Introduction

The embodiments of the invention provide inspection systems and methods for indirect bandgap semiconductor structures, including bare or partially processed wafers. In particular, the systems and methods are particularly suited for testing silicon structures, including bare or partially processed wafers, partially fabricated silicon devices, bare or partially processed silicon-on-insulator (SOT) structures, and fully fabricated silicon devices. The systems and methods are able to contactlessly detect defects existing in the bare wafer prior to processing and throughout various fabrication stages through to the finished semiconductor device, including devices that have been partly metallized. By contactless, what is meant is that no electrical contact is required. For example, the embodiments of the invention can inspect silicon structures and identify defects, which might otherwise result in the structure being a rejected solar cell or other photovoltaic device. The systems and methods are also able to contactlessly determine spatially resolved material parameters, such as local defect densities, local shunts, local current-voltage characteristics, local diffusion length, and local minority carrier lifetime after various processing steps. The embodiments of the invention utilize the photoluminescence (PL) simultaneously induced across large areas of indirect bandgap semiconductor structures to characterize the indirect bandgap semiconductor structures.

In the embodiments of the invention, instead of analyzing the spectral content of the photoluminescence, the spatial variation of a photoluminescence signal is used to obtain information about the quality of the indirect bandgap semiconductor material. As the embodiments of the invention are particularly well suited to use with silicon, the description hereinafter refers to silicon structures, including silicon wafers. However, in the light of this disclosure, those skilled in the art will appreciate that the embodiments of the invention may be practiced with other indirect bandgap semiconductors, such as germanium and alloys of silicon and germanium. The systems and methods for inspecting silicon structures may allow for wafers to be inspected at rates suitable for industrial application (e.g., about 1 wafer per second).

In the embodiments of the invention, light suitable for inducing photoluminescence in silicon is generated and used to illuminate substantially uniformly a large area of a silicon sample. The term "substantially uniform" is used to describe the light, which may equally referred to as homogeneous, since as a practical matter illumination is not perfectly uniform. For example, monochromatic or substantially monochromatic light (e.g. from a laser or laser diode) or partly filtered light from a broad spectrum light source (e.g. a flash lamp) may be used to illuminate the silicon sample. In particular, short-pass filtering is applied to the generated light to greatly reduce the spectral content of the light above a specified wavelength. An optical arrangement is used in combination with the light source to illuminate homogeneously a large area of the wafer. Preferably, the entire wafer area to be investigated is illuminated homogeneously. The photoluminescence induced simultaneously in the silicon structure by the substantially uniform, simultaneous incident light is captured using an image capture device capable of capturing simultaneously the induced photoluminescence. The image capture device preferably comprises a focusing element and a focal plane array of light sensitive electronic elements. The focal plane array of light sensitive electronic elements may comprise a charge coupled device (CCD) array. The focal plane array may be made from silicon. However, as described hereinafter, other devices besides a CCD array may be practiced without departing from the scope and spirit of the invention. The image capture device may be used in combination with optical imaging and/or filtering arrangements.

In some embodiments of the invention, the silicon wafer is illuminated from one side using the noted light source, and the photoluminescence induced in the large area of the wafer by the incident light is captured from the opposite side of the silicon wafer. In other embodiments, the photoluminescence is captured from the same side of the silicon wafer that is illuminated. Imaging and image processing techniques are then applied to the captured PL images. Analyzing the data allows determining local material parameters within the silicon structure using the spatial variation of the photoluminescence induced in the large area. This may allow identifying silicon structures that are defective at an early stage in device manufacturing to reject those structures that will be rejected ultimately.

While the embodiments of the invention are suited for industrial application, the methods and systems can be applied to scientific research. Photoluminescence images may be used for example to determine local defect rich areas, local shunts, local current-voltage characteristics, local diffusion length, and/or local minority carrier lifetime, which may be of benefit not only in photovoltaics, but also in other fields such as microelectronics. The embodiments of the invention can be applied in contactless mode and are therefore particularly suited to inspect local material parameters after individual processing steps. The embodiments of the invention are described in greater detail hereinafter.

2. Inspecting an Indirect Bandgap Semiconductor Structure

Figure 6:
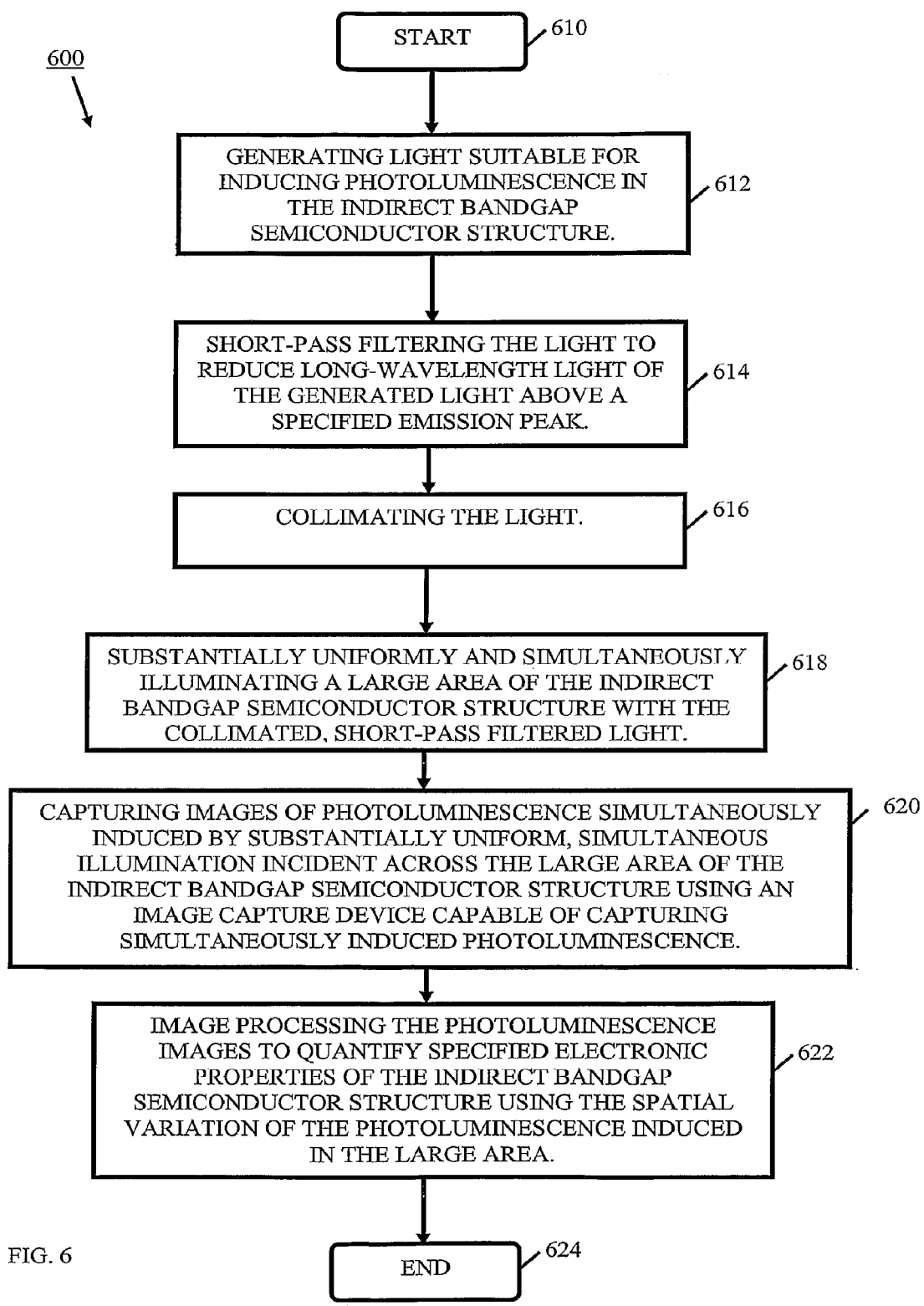
FIG. 6 is a flow diagram of a method of inspecting an indirect bandgap semiconductor structure in accordance with an embodiment of the invention.

FIG. 6 is a high-level flow diagram illustrating a method 600 of inspecting an indirect bandgap semiconductor structure. In step 610, processing commences. In step 612, light suitable for inducing photoluminescence in the indirect bandgap semiconductor structure is generated. In step 614, the light is short-pass filtered to reduce long-wavelength light of the generated light above a specified emission peak. In step 616, the light is collimated. Steps 614 and Step 616 can also be carried out in the reverse order. In step 618, a large area of the indirect bandgap semiconductor structure is substantially uniformly and simultaneously illuminated with the collimated, short-pass filtered light. In step 620, images of photoluminescence simultaneously induced by the substantially uniform, simultaneous illumination incident across the large area of the indirect bandgap semiconductor structure are captured using an image capture device capable of capturing simultaneously the induced photoluminescence. In step 622, the photoluminescence images are image processed to quantify specified electronic properties of the indirect bandgap semiconductor structure using the spatial variation of the photoluminescence induced in the large area. Processing then terminates in step 622. The foregoing method of inspecting an indirect bandgap semiconductor structure is expounded upon hereinafter with reference to several embodiments implementing various systems for inspecting such structures.

3. Illumination and Imaging on Opposite Sides

FIG. 1 illustrates a system 100 for inspecting a silicon structure 140, which is preferably a silicon wafer. Photovoltaic and microelectronic devices can be fabricated in a number of stages on such a silicon wafer. The system 100 of FIG. 1 can be used to inspect a bare or partially processed wafer, a wafer that has undergone any number of processing steps to form a photovoltaic device such as a solar cell or a microelectronic device, and a finished device resulting from the fabrication process. For example, the silicon wafer 140 may have dimensions of 150 mm×150 mm×0.25 mm. The structure may comprise a bare or partially processed silicon-on-insulator (SOI) structure with a substrate that is transparent to the incident light. The inspection method can be performed at room temperature. For ease of discussion, the silicon structure is simply referred to hereinafter as the silicon sample.

The system 100 comprises a light source 110, a short-pass filter unit 114, and an image capture device 122. The short-pass filter unit 114 may comprise one or more short-pass filters. A short-pass filter passes through the excitation light and absorbs or reflects an unwanted long wavelength emission(s). Examples of short-pass filters include colored filters and dielectric interference filters. Alternatively, a dielectric mirror may be used (e.g. under 45 degrees) that reflects that part of the light that is to be used and transmits the unwanted long wavelength light. The short-pass filter unit may also comprise a combination of short pass filters and dielectric mirrors.

The system also comprises a collimator 112 and may comprise a homogenizer 116, which is a device for converting a collimated beam of light that has non-uniform intensity into a uniformly illuminated region of a plane perpendicularly incident to the collimated beam. Examples include cross cylindrical lens array(s) and a micro lens array. A collimator may be lenses of various sorts. In the embodiment of FIG. 1, the elements of the system 100 are arranged as follows: a light source 110 facing the silicon sample 140, the collimator 112, the short-pass filter unit 114, and the homogenizer 116 optically aligned in that sequence. In another embodiment of the invention, the ordering of the collimator 112 and the short-pass filter unit 114 may be reversed. A field lens 117 may be used between the homogenizer and the silicon sample. The elements are spaced apart from the silicon sample 140 so that a large area of the sample 140 can be illuminated homogeneously.

The light source 110 generates light suitable for inducing simultaneously photoluminescence across a large area of the silicon sample 140. The total optical power of the generated light may exceed 1.0 Watt. Light sources of higher power are able to more quickly and intensely induce photoluminescence in the silicon sample 140. The light source 110 may generate monochromatic or substantially monochromatic light. The light source 110 may be at least one laser. For example, an 808 nm diode laser may be used to generate monochromatic light. Two or more lasers with different principal wavelengths may also be practiced. Another light source 110 may comprise a broad spectrum light source (e.g., a flash lamp) combined with suitable filtering to provide partly filtered light. Still another light source 110 may be a high-powered light emitting diode (LED). Yet another light source 110 may comprise an array of light emitting diodes (LED). For example, such an LED array may comprise a large number (e.g. 60) of LEDs in a compact array with heatsinking. Other high powered light sources may be practiced without departing from the scope and spirit of the invention.

The light from the light source 110 is collimated into parallel beams by a collimator or collimator unit 112, which may comprise more than one element. Short-pass filtering is applied to the generated light. This may be done using an interference short-pass filter unit 114 comprising one or more filter elements. Short-pass filtering the generated light reduces long-wavelength light above a specified emission peak. The short-pass filter 114 may reduce by a factor of about 10 or more the total photon flux in a long-wavelength tail of the generated light. The long-wavelength tail may begin at a wavelength that is about ten percent (10%) higher than a longest wavelength emission peak of the light source 110. For example, the filtering may remove unwanted spectrum components such as infra-red components with wavelengths in the range of 900 nm to 1800 nm or a subrange of that range. Multiple short-pass filters may be used because one filter may not be sufficient itself to remove or reduce unwanted spectrum components. The short-pass filters may be implemented at numerous different positions in the overall combination of optical elements between the light source 110 and the silicon sample 140. For example, filters may be positioned between the homogenizer 116 and the field lens 117. If more than one short pass filter is used, then one or more of the filters may be arranged so that they are tilted under some angle against the optical axis of the collimated beam to avoid multiple reflections of the reflected light. The short-pass filtered and collimated light may then be homogenized by a homogenizer 116 to homogeneously illuminate a large area of the silicon sample 140. However the ordering of the steps may be altered. The homogeneously illuminated area of the silicon sample may be greater than or equal to about 1.0 cm$^2$. The homogenizer 116 distributes the collimated beams evenly across the surface of the silicon sample 140.

The homogeneous illumination incident on the surface of the silicon sample 140 is sufficient to induce photoluminescence simultaneously in the silicon sample. This photoluminescence is represented in FIG. 1 by arrows or rays emanating from the opposite surface of the silicon sample 140. For ease of illustration only, corresponding photoluminescence is not shown emanating from the first surface of the silicon sample 140 that the light source 110 is oriented towards. The external photoluminescence quantum efficiency of silicon can be very low (of the order of $<10^{-6}$). An image capture device 130 captures images of the photoluminescence simultaneously induced in the silicon sample. The short pass filter unit 114 reduces or removes incident light from the light source 110 from being received by the image capture device 130. Light source tail radiation may be of the order of $10^{-4}$ of a source peak, which can significantly exceed the PL efficiency of silicon (of the order of $10^{-6}$) in contrast to that of direct bandgap semiconductors like AlGaAs (of the order of $10^{-2}$). In this embodiment, the light source 110 is oriented toward the surface of one side of the silicon sample 140 for illumination of that surface. The silicon sample 140 acts as long-pass filter of the generated light illuminating the silicon sample 140. The image capture device 130 is oriented toward the surface of the opposite side of the silicon sample 140 for capturing the PL images from that opposite side. A long-pass filter unit 118 may be used in combination with the image capture device 130. This filter unit 118 may be optional, since the silicon wafer 140 may remove any residual light from the light source 110 dependent upon the wafer thickness and wavelengths of incident light. The image capture device 130 (and the long-pass filter 118) is suitably spaced apart from the other surface that the image capture device 130 is facing.

The image capture device 130 comprises a focusing element 120 (e.g. one or more lenses) and a focal plane array 122 of light sensitive electronic elements. In this embodiment, the focal plane array 122 of light sensitive electronic elements comprises an array of charge coupled devices (CCD). The focal plane array may be made of silicon and may be cooled. Cooling improves the signal-to-noise ratio of such a focal plane array. For example, the image capture device 130 may be a digital video camera having a silicon CCD array and be provided with a digital interface (e.g., USB or Firewire) or storage media (e.g., a DV tape or memory stick) for communication of recorded images. Alternatively, the focal plane array 122 of light sensitive electronic elements may be made from InGaAs. As described hereinafter with reference to other embodiments of the invention, the image capture device 130 may comprise a pixel detector. The pixel detector may be a contact pixel detector coupled to the opposite surface of the silicon sample. Alternatively, the image capture device 130 may comprise a pixel detector or an array of charge coupled devices (CCD) and a tapered fiber bundle that is coupled between the opposite surface of the silicon sample 140 and the pixel detector or CCD array 140 or a CCD in contact mode. Other image capture devices may be practiced provided the devices are capable of capturing simultaneously the induced photoluminescence across a large area of the semiconductor sample.

Image processing techniques may be applied to the PL images to quantify specified electronic properties of the silicon sample 140. Spatial variations of the PL intensity are checked for. As shown in FIG. 1, a general-purpose computer 150 can acquire and analyze PL images recorded by the image capture device 130 via a communications channel 152, which may be a suitable communications interface or storage device. The image processing techniques may be implemented in software, hardware, or a combination of the two. The specified electronic properties may comprise one or more of local defect rich areas, local shunts, local current-voltage characteristics, local diffusion length and local minority carrier lifetime. The embodiments of the invention are able to determine such properties contactlessly. Imaging is distinct from photoluminescence mapping, which is slow and therefore not suitable for industrial application as an inline production tool, and spectroscopic testing of PL, which typically involves testing a small area of a semiconductor. The system in accordance with this embodiment of the invention can be used to identify defective areas of the wafer 140. The embodiments of the invention can be used to contactlessly test using photoluminescence the silicon structure after each step of processing of a photovoltaic device. An influence of individual processing steps on the spatial material quality can thereby be monitored.

Figure 4:
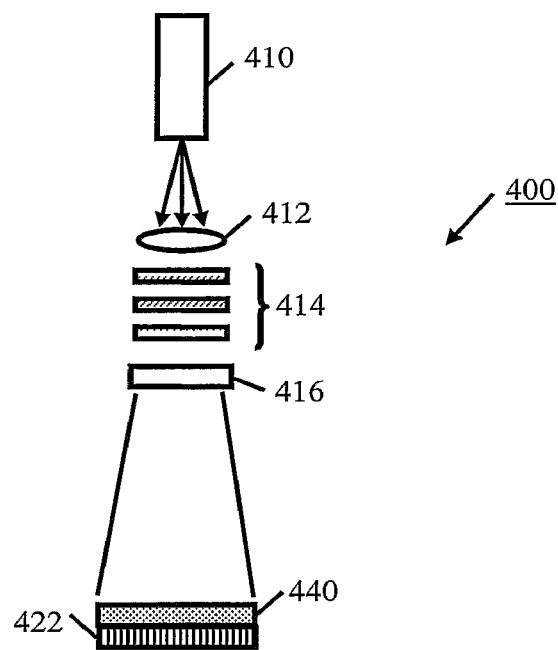
FIG. 4 is a block diagram of a system for inspecting an indirect bandgap semiconductor structure in accordance with yet another embodiment of the invention.

FIG. 4 illustrates a system 400 for inspecting a silicon structure 440 in accordance with a further embodiment of the invention. In the drawing, features of FIG. 4 that are like those of FIG. 1 are given a like reference numeral (e.g. the light source 110 of FIG. 1 and the light source 410 of FIG. 4 have such like reference numerals). The structure 440 is again preferably a silicon wafer. To simplify the drawing, a general-purpose computer is not shown. The system 400 comprises a light source 410, a short-pass filter unit 414, and an image capture device 422. The system also comprises a collimator 412 and may comprise a homogenizer 416. A field lens may also be employed (not shown).

Again, the light source 410 generates light suitable for inducing photoluminescence simultaneously across a large area of the silicon sample 440. The power of the generated light exceeds 1.0 Watt. Light sources 410 that can be practiced comprise one or more lasers, a broad spectrum light source combined with suitable filtering to provide partly filtered light, and an array of light emitting diodes (LED). Other high powered light sources may be practiced without departing from the scope and spirit of the invention.

In this embodiment, the image capture device comprises a pixel detector 422 and in particular a contact pixel detector 422 coupled to the surface of the silicon sample 440 that is opposite the illuminated surface. The contact pixel detector 422 detects photoluminescence induced simultaneously across a large area of the silicon sample 440. The contact pixel detector 422 may have a higher efficiency of collecting photoluminescence than the image capture device of FIG. 1. Further the contact pixel detector 422 may have a lower resolution than the CCD array of FIG. 1. Also, a long-pass filter may not be required between the sample 440 and the contact pixel detector 422. The silicon sample 440 may perform this function.

Figure 5:
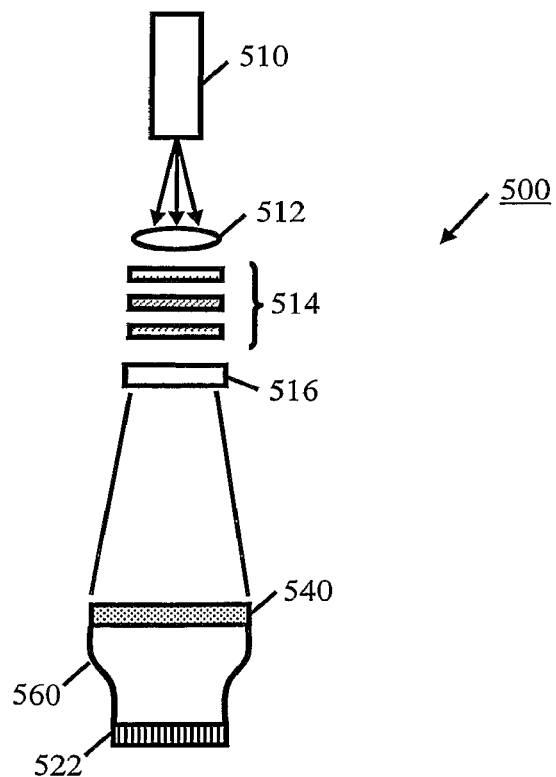
FIG. 5 is a block diagram of a system for inspecting an indirect bandgap semiconductor structure in accordance with a further embodiment of the invention.

FIG. 5 illustrates another system 500 for inspecting a silicon structure 540 in accordance with another embodiment of the invention. Again, features of FIG. 5 that are like those of FIG. 1 are given a like reference numeral. The structure 540 comprises preferably a silicon wafer. To simplify the drawing, a general-purpose computer is again not shown. The system 500 comprises a light source 510, a short-pass filter unit 514, and an image capture device 522. The system also comprises a collimator 512 and may comprise a homogenizer 516.

In this embodiment, the image capture device comprises a pixel detector or an array of charge coupled devices (CCD) 522, which is coupled by a tapered fiber bundle 560 to the surface of the silicon sample 540 that is opposite the illuminated surface. The tapered fiber bundle 560 may reduce the area of the CCD array relative to the sample size by a factor of 2 to 3, up to about 10. For example, the CCD array or pixel detector may have a size of 60 mm×60 mm.

4. Illumination and Imaging on Same Side

Figure 2:
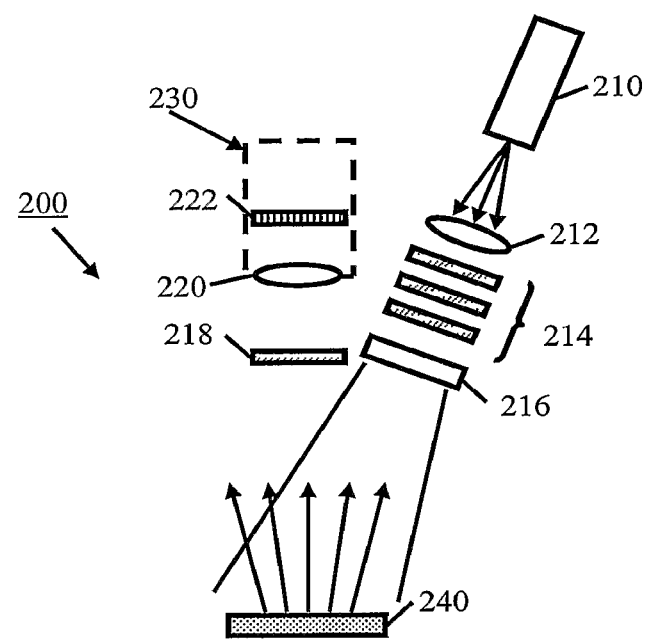
FIG. 2 is a block diagram of a system for inspecting an indirect bandgap semiconductor structure in accordance with another embodiment of the invention.

FIG. 2 illustrates a system 200 for inspecting a silicon structure 240 in accordance with still another embodiment of the invention. In the drawing, features of FIG. 2 that are like those of FIG. 1 are given a like reference numeral. The structure 240 is again preferably a silicon wafer. To simplify the drawing, a general-purpose computer is not shown. The system 200 comprises a light source 210, a short-pass filter unit 214, and an image capture device 230. The system 200 also comprises a collimator 212 and may comprise a homogenizer 216. A field lens (not shown) may also be employed.

Again, the light source 210 generates light suitable for inducing photoluminescence homogeneously across a large area of the silicon sample 240. The total optical power of the generated light exceeds 1.0 Watt. Any of a number of light sources may be employed as the light source 210. Details of such light sources are set forth hereinbefore with reference to FIG. 1.

In the embodiment of FIG. 2, the elements of the system 200 are arranged as follows: a light source 210 facing the silicon sample 240, the collimator 212, the short-pass filter unit 214, and the homogenizer 216 optically aligned in that sequence. However, other orderings of some or all of these elements may be practiced without departing from the scope and spirit of the invention. This combination of lighting elements is off-axis in that the light source 210 and associated optical elements are oriented at the surface of the sample 240 at an angle of less than 90 degrees. The elements are together spaced apart from the silicon sample 240 so that the large area of the sample 240 can be illuminated. The image capture device 230 (and a long-pass filter unit 218) is perpendicularly oriented relative to the surface of the silicon sample 240. The long-pass filter unit 218 is needed to remove incident light from the light source 210. Thus, the image capture device 230 captures photoluminescence from the same side as that illuminated by incident light from the light source 210 to induce the photoluminescence (again indicated by rays or arrows emanating from the surface of the silicon sample 240).

The light source 210 generates light suitable for inducing photoluminescence in the silicon sample. The total optical power of the generated light exceeds 1.0 Watt.

The image capture device 130 in this embodiment comprises a focusing element 220 (e.g. a lens) and a focal plane array 222 of light sensitive electronic elements. In this embodiment, the focal plane array 222 of light sensitive electronic elements comprises an array of charge coupled devices (CCD). Preferably, the focal plane array may be made from silicon and may be cooled. For example, the image capture device 130 may be a digital video camera having a silicon CCD array and be provided with a digital interface (e.g., USB or Firewire) or storage media (e.g., a DV tape or memory stick) for communication of recorded images. Alternatively, the focal plane array 222 of light sensitive electronic elements may be made from InGaAs. As described hereinafter with reference to other embodiments of the invention, the image capture device 230 may comprise a pixel detector.

Image processing techniques may be applied to the PL images to quantify specified electronic properties of the silicon sample 240 using the spatial variation of the photoluminescence induced in the large area. The specified electronic properties may comprise one or more of local defect rich areas, local shunts, local current-voltage characteristics, and local minority carrier lifetime.

Figure 3:
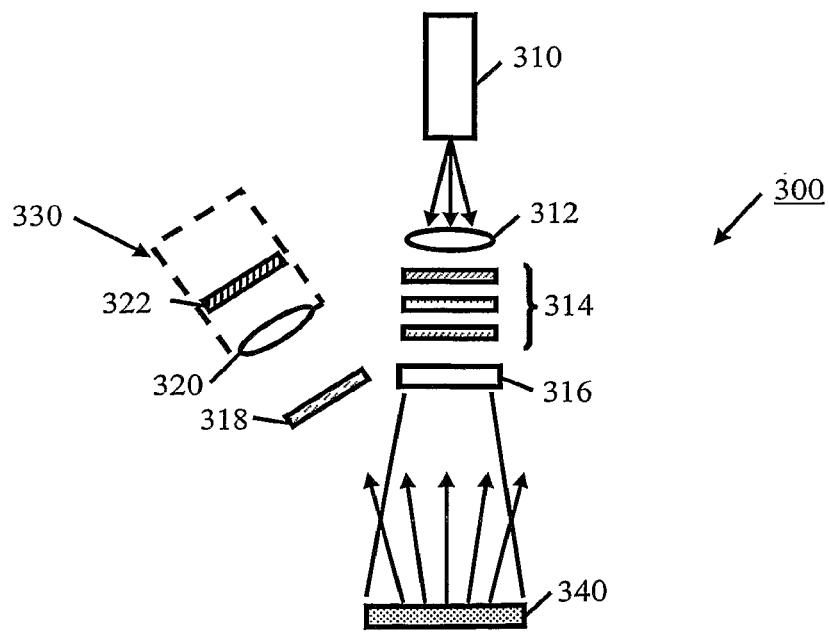
FIG. 3 is a block diagram of a system for inspecting an indirect bandgap semiconductor structure in accordance with a further embodiment of the invention.

FIG. 3 illustrates a system 300 for inspecting a silicon structure 340 in accordance with yet another embodiment of the invention. This system 300 also comprises a light source 310, a short-pass filter unit 314, and an image capture device 330. The system 300 also comprises a collimator 312 and may comprise a homogenizer 316. The system may also comprise a field lens (not shown). The image capture device 330 may comprise a focusing element 320 (e.g. a lens) and a focal plane array 322 of light sensitive electronic elements. A long-pass filter unit 318 may also be disposed between the camera 330 and the surface from which the photoluminescence emanates. The elements of the system 300 are the same as those in FIG. 2, except that the light source 310 and associated optical elements are perpendicularly oriented to the surface of the sample 340. The image capture device 330 (and the long-pass filter unit 318) is off-axis in that the image capture device 330 (and the long-pass filter unit 318) is oriented at the surface of the sample 340 at an angle of less than 90 degrees. The image capture device 330 captures photoluminescence from the same side as that illuminated by the light source 310 to induce the photoluminescence (again indicated by rays or arrows) emanating from the surface of the silicon sample 340.

Figure 7:
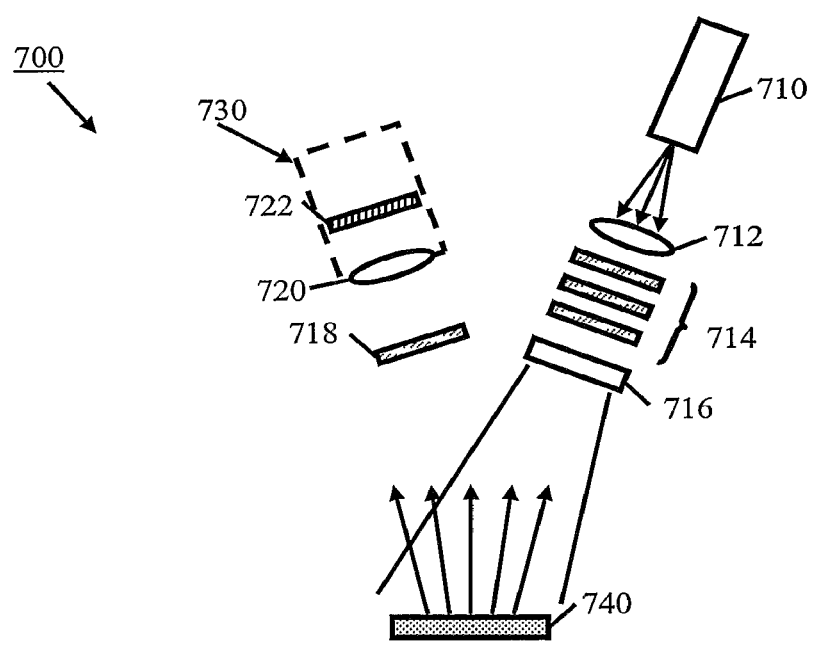
FIG. 7 is a block diagram of a system for impacting an indirect bandgap semiconductor structure in accordance with still another embodiment of the invention.

FIG. 7 illustrates a system 700 for inspecting a silicon structure 740, like that of FIGS. 2 and 3, except that in this embodiment, the light source 710 and associated optics 712, 714, 716 and the image capture system 730, 722, 720, 718 are both off-axis (not perpendicular) to the sample 740.

The embodiments of the invention can be used advantageously with indirect bandgap semiconductors, which do not generate photoluminescence as efficiently as direct bandgap semiconductors like GaAs, AlGaAs and many III-V semiconductors. Large areas including up to the entire area of a wafer can be illuminated to induce photoluminescence simultaneously. Advantageously, the entire wafer is simultaneously illuminated, which permits faster and more consistent testing. For example, a solar cell normally operates when the entire device is illuminated, not just a part of the solar cell. More quantitative details of the cell can be obtained in this fashion. While the embodiments of the invention have been described with reference to inspecting wafers to identify defects in the wafers, the embodiments of the invention are not limited to such applications. The embodiments of the invention can be used to inspect partially or fully formed devices to identify defects in the devices. The embodiments of the invention have more general application to the microelectronics industry.

The embodiments of the invention where the light source and image capture system are on opposite sides or the same side of the indirect bandgap semiconductor structure may be used for identifying possible defects in bare wafers and partially fabricated semiconductor devices. The same-side light source and image capture system configuration may be used to test fully fabricated semiconductor devices, especially where one surface of the device is fully metallized.

The foregoing describes only a small number of methods and systems for inspecting indirect bandgap semiconductors in accordance with embodiments of the invention. Modifications and/or substitutions can be made thereto without departing from the scope and spirit of the invention. The embodiments are intended to be illustrative and not restrictive.

We claim:

1. A method of analyzing an indirect bandgap semiconductor material, said method comprising the steps of:
    generating substantially monochromatic light suitable for inducing photoluminescence in said indirect bandgap semiconductor material;
    short-pass filtering said substantially monochromatic light to reduce long-wavelength light of said generated light above a predetermined emission peak;
    collimating said substantially monochromatic light;
    illuminating said indirect bandgap semiconductor material with said collimated, short-pass filtered substantially monochromatic light to induce a measurable photoluminescence signal from said indirect bandgap semiconductor material; and
    capturing, with an image capture device, an image of photoluminescence of the indirect bandgap semiconductor material, from which information on one or more material properties of said indirect bandgap semiconductor material can be obtained, induced in a large area of said indirect bandgap semiconductor material by the illumination,
    wherein said material properties are at least one of shunts, current-voltage characteristics, diffusion lengths and minority carrier lifetimes.

2. A method as claimed in claim 1, further comprising a step of processing said image to determine spatial variations of luminescence in said image.

3. A method as claimed in claim 2, wherein said processing of said image comprises determining spatial variations of said one or more material properties of said indirect bandgap semiconductor material using spatial variations in said image.

4. A method as claimed in claim 2, wherein said processing step is effected within about 1 second.

5. A method as claimed in claim 2, wherein any one of said illuminating, capturing and processing steps is conducted in-line on a production process.

6. A method as claimed in claim 1, wherein said illumination is substantially homogeneous across said area.

7. A method as claimed in claim 1, wherein said short-pass filtering substantially removes components in a wavelength range of said photoluminescence.

8. A method as claimed in claim 1, wherein light incident on said image capture device is long pass filtered to substantially prevent said illumination from being imaged.

9. A method as claimed in claim 1, wherein said illumination is applied to one side of said indirect bandgap semiconductor material, and
    wherein said image capture device captures photoluminescence emitted from an opposite side of said indirect bandgap semiconductor material that is generated by said illumination of said one side, such that said indirect bandgap semiconductor material serves as a long pass filter to substantially prevent said illumination from being imaged.

10. A method as claimed in claim 1, wherein said illuminating of said indirect bandgap semiconductor material is performed for up to 1 second.

11. A method as claimed in claim 1, wherein said illuminating and capturing steps are effected within about 1 second.

12. A method as claimed in claim 1, wherein the method is applied to an indirect bandgap semiconductor material selected from the group consisting of: a silicon structure, a bare or partially processed wafer, a bare or partially processed Silicon-On-Insulator (SOI) structure, a fully fabricated silicon device and a solar cell.

13. A method as claimed in claim 1, wherein said area is at least 1 cm$^2$.

14. A method as claimed in claim 1, wherein said area comprises an entire side of said indirect bandgap semiconductor material.

15. A method as claimed in claim 1, wherein at least said illuminating and capturing steps are performed while said indirect bandgap semiconductor material is at room temperature.

16. In a multi-step process for producing semiconductor devices from an indirect bandgap semiconductor material, a method of analyzing one or more material properties of said indirect bandgap semiconductor material, said method comprising the steps of:
    generating substantially monochromatic light suitable for inducing photoluminescence in said indirect bandgap semiconductor material;
    short-pass filtering said substantially monochromatic light to reduce long-wavelength light of said generated light above a predetermined emission peak;
    collimating said substantially monochromatic light;
    illuminating said indirect bandgap semiconductor material with said collimated, short-pass filtered substantially monochromatic light to induce a measurable photoluminescence signal from said indirect bandgap semiconductor material; and
    capturing an image of photoluminescence of the indirect bandgap semiconductor material, from which information on said one or more material properties can be obtained, induced in a large area of said indirect bandgap semiconductor material by the illumination; and
    processing spatial variations in said image to determine spatial variations of said one or more material properties,
    wherein said illuminating, capturing and processing steps are conducted within a predetermined production step of said process, and
    wherein said material properties are at least one of shunts, current-voltage characteristics, diffusion lengths and minority carrier lifetimes.

17. A method for analyzing one or more material properties of an indirect bandgap semiconductor material in a process for producing a semiconductor device from said indirect bandgap semiconductor material, said method comprising the steps of:
- generating substantially monochromatic light suitable for inducing photoluminescence in said indirect bandgap semiconductor material;
- short-pass filtering said substantially monochromatic light to reduce long-wavelength light of said generated light above a predetermined emission peak;
- collimating said substantially monochromatic light;
- illuminating said indirect bandgap semiconductor material with said collimated, short-pass filtered substantially monochromatic light to induce a measurable photoluminescence signal from said indirect bandgap semiconductor material; and
- capturing an image of photoluminescence of the indirect bandgap semiconductor material, from which information on said one or more material properties can be obtained, induced in a large area of said indirect bandgap semiconductor material by the illumination; and
- processing said image to determine spatial variations of said one or more material properties,
- wherein said method is applied to said indirect bandgap semiconductor material at any point between said indirect bandgap semiconductor material being a bare wafer and a completed device, and
- wherein said material properties are at least one of shunts, current-voltage characteristics, diffusion lengths and minority carrier lifetimes.

18. A system for analyzing an indirect bandgap semiconductor material, said system comprising:
- a light source generating substantially monochromatic light for illuminating said indirect bandgap semiconductor material with light suitable for inducing photoluminescence from said indirect bandgap semiconductor material;
- a short-pass filter that reduces long-wavelength light of said substantially monochromatic light above a predetermined emission peak;
- a collimator for collimating said substantially monochromatic light;
- wherein said collimated, short-pass filtered substantially monochromatic light illuminates said indirect bandgap semiconductor material for inducing a measurable photoluminescence signal from said indirect bandgap semiconductor material; and
- an image capture device for capturing an image of photoluminescence of the indirect bandgap semiconductor material, from which information on one or more material properties of said indirect bandgap semiconductor material can be obtained, induced in a large area of said indirect bandgap semiconductor material by the illumination,
- wherein said material properties are at least one of shunts, current-voltage characteristics, diffusion lengths and minority carrier lifetimes.

19. A system as claimed in claim 18, further comprising a processor configured to determine spatial variations of luminescence in said image.

20. A system as claimed in claim 19, wherein said processor is configured to determine spatial variations of said one or more material properties of said indirect bandgap semiconductor material using spatial variations in said image.

21. A system as claimed in claim 18, wherein said system is configured to illuminate said area substantially homogeneously.

22. A system as claimed in claim 18, wherein said short pass filter is disposed between said light source and said indirect bandgap semiconductor material, for substantially removing components of said illumination in a wavelength range of said photoluminescence.

23. A system as claimed in claim 18, further comprising a long pass filter disposed between said indirect bandgap semiconductor material and said image capture device substantially preventing said substantially monochromatic light from reaching said image capture device.

24. A system as claimed in claim 18, wherein said light source illuminates one side of said indirect bandgap semiconductor material,
- wherein said image capture device captures photoluminescence emitted from an opposite side of said indirect bandgap semiconductor material that is generated by said illumination of said one side, and
- wherein said indirect bandgap semiconductor material substantially prevents said substantially monochromatic light from reaching said image capture device.

25. A system as claimed in claim 18, wherein said system is adapted to illuminate said area for about 1 second or less.

26. A system as claimed in claim 18, wherein said light source and said image capture device are adapted to illuminate said indirect bandgap semiconductor material and capture said image within about 1 second.

27. A system as claimed in claim 18, wherein said system is located in-line on a production process.

28. A system as claimed in claim 18, wherein said system is adapted to analyze an indirect bandgap semiconductor material selected from the group consisting of: silicon, a bare or partially processed wafer, a bare or partially processed Silicon-On-Insulator (SOI) structure, a fully fabricated silicon device and a solar cell.

29. A system as claimed in claim 18, wherein said system is adapted to capture an image of photoluminescence induced in at least 1 cm$^2$ of said indirect bandgap semiconductor material.

30. A system as claimed in claim 18, wherein said system is adapted to capture an image of photoluminescence induced in the entire area of one side of said indirect bandgap semiconductor material.

31. In a multi-step process for producing semiconductor devices from an indirect bandgap semiconductor material, a system for analyzing one or more material properties of said indirect bandgap semiconductor material, said system comprising:
- a light source generating substantially monochromatic light for illuminating said indirect bandgap semiconductor material with light suitable for inducing photoluminescence from said indirect bandgap semiconductor material;
- a short-pass filter that reduces long-wavelength light of said substantially monochromatic light above a predetermined emission peak;
- a collimator for collimating said substantially monochromatic light;
- wherein said collimated, short-pass filtered substantially monochromatic light illuminates said indirect bandgap semiconductor material for inducing a measurable photoluminescence signal from said indirect bandgap semiconductor material; and
- an image capture device for capturing an image of photoluminescence of the indirect bandgap semiconductor material, from which information on said one or more material properties can be obtained, induced in a large area of said indirect bandgap semiconductor material by the illumination; and a processor for processing spatial variations in said image to determine spatial variations of said one or more material properties, wherein said material properties are at least one of shunts, current-voltage characteristics, diffusion lengths and minority carrier lifetimes.

32. A multi-step process line for producing an indirect bandgap semiconductor device, said process line comprising one or more systems according to claim 31 located at one or more positions in said process line.

* * * * *